US011434448B2

(12) United States Patent
Blondeau et al.

(10) Patent No.: US 11,434,448 B2
(45) Date of Patent: *Sep. 6, 2022

(54) PERFUME COMPOSITIONS

(71) Applicant: Givaudan S.A., Vernier (CH)

(72) Inventors: Philippe Blondeau, Paris (FR); Alice Bresson Boil, Herblay (FR)

(73) Assignee: Givaudan S.A., Vernier (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/081,005

(22) Filed: Oct. 27, 2020

(65) Prior Publication Data

US 2021/0040415 A1 Feb. 11, 2021

Related U.S. Application Data

(60) Continuation of application No. 16/522,024, filed on Jul. 25, 2019, now Pat. No. 10,899,995, which is a division of application No. 15/837,639, filed on Dec. 11, 2017, now Pat. No. 10,407,644, which is a continuation of application No. 15/457,537, filed on Mar. 13, 2017, now Pat. No. 9,868,923.

(30) Foreign Application Priority Data

Mar. 14, 2016 (GB) .................................. 1604290

(51) Int. Cl.
| | |
|---|---|
| *C11B 9/00* | (2006.01) |
| *A01N 25/18* | (2006.01) |
| *A01N 27/00* | (2006.01) |
| *A01N 49/00* | (2006.01) |
| *A61L 9/013* | (2006.01) |

(52) U.S. Cl.
CPC ............ *C11B 9/0019* (2013.01); *A01N 25/18* (2013.01); *A01N 27/00* (2013.01); *A01N 49/00* (2013.01); *A61L 9/013* (2013.01); *C11B 9/0003* (2013.01); *C11B 9/0015* (2013.01); *A61L 2209/13* (2013.01)

(58) Field of Classification Search
CPC ....... C11B 9/00; C11B 9/0003; C11B 9/0015; C11B 9/0019
See application file for complete search history.

(56) References Cited

U.S. PATENT DOCUMENTS

| | | |
|---|---|---|
| 8,501,247 B2 | 8/2013 | Enan et al. |
| 9,492,490 B1 | 11/2016 | Enan |
| 2004/0163542 A1 | 8/2004 | Huang |
| 2009/0018212 A1 | 1/2009 | Einstein et al. |
| 2011/0135764 A1 | 6/2011 | Enan |
| 2012/0097754 A1 | 4/2012 | Vlad et al. |
| 2015/0080265 A1* | 3/2015 | Elzinga ................. A23L 27/202 506/15 |
| 2017/0073614 A1 | 3/2017 | Alchenberger et al. |
| 2017/0094963 A1 | 4/2017 | Enan et al. |

FOREIGN PATENT DOCUMENTS

| | | |
|---|---|---|
| CN | 203564579 U | 4/2014 |
| CN | 102550610 B | 12/2014 |
| JP | S60 53148 A | 3/1985 |
| JP | H 04139104 A | 5/1992 |
| JP | 2001 178808 A | 7/2001 |
| JP | 2009189765 A | 8/2009 |
| JP | 2010 023033 A | 2/2010 |
| KR | 20080081633 A | 9/2008 |
| KR | 20120042009 A | 5/2012 |
| KR | 101177305 B1 | 8/2012 |
| KR | 20140038690 A | 3/2014 |
| KR | 101439385 B1 | 9/2014 |
| WO | WO 2015/181257 A2 | 12/2015 |

OTHER PUBLICATIONS

Search Report, Great Britain Application Serial No. GB1604290.5, dated Aug. 26, 2016.
PCT/EP2017/055783—International Search Report, dated May 31, 2017.
PCT/EP2017/055783—International Written Opinion, dated May 31, 2017.
PCT/EP2017/055783—International Preliminary Report on Patentability, dated Sep. 18, 2018.

* cited by examiner

*Primary Examiner* — Arrie L Reuther
(74) *Attorney, Agent, or Firm* — Curatolo Sidoti & Trillis Co., LPA; Salvatore A Sidoti; Floyd Trillis III

(57) ABSTRACT

A perfume composition having controlled release of phytoncides in an atmosphere in order to generate an air condition resembling the air environment of a forest is provided. The perfume composition includes a) at least about 0.6% by weight of at least one phytoncide; and b) a perfume mixture including (i) at least one solvent; and (ii) at least one fragrance ingredient. At least about 25% by weight of the at least one phytoncide is selected from the group consisting of pinene alpha, pinene beta and combinations thereof.

17 Claims, No Drawings

PERFUME COMPOSITIONS

The present application is a continuation of co-pending U.S. Ser. No. 16/522,024, filed Jul. 25, 2019, which is a divisional of U.S. Ser. No. 15/837,639, filed Dec. 11, 2017, now U.S. Pat. No. 10,407,644 B2, which is a continuation of U.S. Ser. No. 15/457,537, filed Mar. 13, 2017, now U.S. Pat. No. 9,868,923 B2, which claims priority from Great Britain Application Ser. No. 1604290.5, filed Mar. 14, 2016, and which are incorporated herein by reference.

TECHNICAL FIELD

The present disclosure relates to air fresheners. In particular, the present disclosure relates to air freshener perfume compositions providing enhanced and controlled release of phytoncides in an atmosphere. More particularly, the present disclosure relates to air freshener perfume compositions providing a constant release of phytoncides in an atmosphere to generate an air condition resembling the air environment in a forest.

BACKGROUND

Using devices, such as active and passive air fresheners, including electrical plug-in air fresheners, candles, aerosol diffusers, sprays, membrane air fresheners and the like, to deliver nice and refreshing fragrances to air within a room is well known. There are numerous devices of this kind available on the market place, with a number of fragrances available as well. The targeted consumer benefits include, for example, pleasantness of the neighbor odor, hedonics, malodor counteracting, and insect repellency.

Forest bathing, which is a popular exercise in Asian countries, is a means of body sculpting, which includes taking walks and doing aerobic exercises in a forest. It is believed that forest bathing trips have a positive impact on human beings, such as stress and anxiety relief, calming and reinvigorating actions. It is recognized that these benefits are related to the presence of phytoncides or wood oil essence components in the atmosphere of forests. In particular, a correlation between the presence of phytoncides and the activity of the human natural killer cells has been documented. See for example Q. Li at al. International Journal of Immunopathology and Pharmacology 22 (2009) pages 951 to 959 and references cited therein. The enhancement of the natural defense of the organism induced by the exposure of individuals to the atmosphere of natural forests, especially those populated by resinous trees or Eucalyptol trees is also well known. These phytoncides are volatile molecules of the terpene and sesquiterpene families, which are produced by the wood itself, whereas such a production is especially important in resinous trees, such as pine trees and cypress trees.

However, people are busy with work and often do not have the time to travel to a forest to enjoy the air environment in a forest, especially, the inhabitants in the cities. Accordingly, there remains a need to provide an air freshener device, which generates and delivers the health and therapeutic benefits of forest air to the inside environment.

SUMMARY

In one embodiment, a perfume composition having controlled release of phytoncides in an atmosphere in order to generate an air condition resembling the air environment of a forest includes a) at least about 0.6% by weight of at least one phytoncide; and b) a perfume mixture including (i) at least one solvent; and (ii) at least one fragrance ingredient. At least about 25% by weight of the at least one phytoncide is selected from the group consisting of pinene alpha, pinene beta and combinations thereof.

In another embodiment, an air freshener device includes a perfume composition having controlled release of phytoncides in an atmosphere in order to generate an air condition resembling the air environment of a forest. The perfume composition includes (a) at least about 0.6% of at least one phytoncide selected from the group consisting of pinene alpha, pinene beta, and combinations thereof and (b) a perfume mixture including (i) at least one solvent; and (ii) at least one fragrance ingredient. The perfume composition has a phytoncide evaporation rate of from about 0.8 µg/m3 per hour to about 10 µg/m3 per hour that is relatively constant for at least 30 days.

In another embodiment, an automatic aerosol air freshener device includes a perfume composition having controlled release of phytoncides in an atmosphere in order to generate an air condition resembling the air environment of a forest. The perfume composition includes at least one phytoncide selected from the group consisting of pinene alpha, pinene beta and combinations thereof. The perfume composition has a phytoncide evaporation rate of from about 0.8 µg/m3 per hour to about 10 µg/m3 per hour that is relatively constant for at least at least 30 days.

These and other features, aspects and advantages of specific embodiments will become evident to those skilled in the art from a reading of the present disclosure.

DETAILED DESCRIPTION

The following text sets forth a broad description of numerous different embodiments of the present disclosure. The description is to be construed as exemplary only and does not describe every possible embodiment since describing every possible embodiment would be impractical, if not impossible. It will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims. All publications and patents cited herein are incorporated herein by reference.

A phytoncide is a biologically active substance of plant origin that kills or inhibits the growth and development of bacteria, microscopic fungi and insects. Phytoncides play an important role in plant immunity. They were discovered by B. P. Tokin in 1928. The ability to produce phytoncides is a quality common to all plants that was acquired in the process of their historical development. The secretion of phytoncides increases when the plant is injured. Various clinical studies conducted mainly in Japan demonstrate that the phytoncides also have a positive action on human health.

Phytoncides vary in chemical composition. They usually consist of groups of compounds such as glycosides, terpenoids, tannin components, phytoalexins, sophoraflavone, alpha.mangostin and stilbene oligomers. However, the portion of interest for air freshener application is the one including phytoncides having a vapour pressure higher than about 0.001 mm/Hg at 25° C., in another embodiment higher than about 0.01 mm/Hg at 25° C., and in another embodiment higher than about 0.1 mm/Hg at 25° C. Non-limiting examples of such phytoncides include mono-terpenes, such as limonene, alpha-pinene, beta-pinene, beta-myrcene, tricyclene, camphene, delta-3-carene, 2-carene, alpha-terpinene, gamma-terpinene, terpinolene, camphor, camphene, para-cymene, alpha-phellandrène, beta-phellandrene, sabinene, cis-ocimene, beta-ocimene, alpha-thujene, beta-elemene, bornene; and sesquiterpenes, such as farnesene, copaene, caryophyllene, alpha-longifolene, alpha-cedrene, gamma-muurolene, delta-cadinene; and their derivatives, such as elemol, cedrol, alpha-eudesmol and the like.

More generally, any hydrocarbon derived from isopentenyl pyrophosphate, via biosynthetic pathways involving either the condensation of isopentenyl pyrophosphate with dimethylallyl pyrophosphate into geranyl pyrophosphate and farnesyl pyrophosphate, or the reaction between isopentenyl pyrophosphate and the isoprene synthase enzyme, are of interest for the sake of the present disclosure.

Natural emission levels of phytoncides may be variable and depend on tree species and whether the emission is assessed during day time or during night time. For example, it is known that the highest concentration of terpenes in forest atmosphere is found at around 4 am. For example, R. Janson, J. Atmospheric Chemistry 14 (1992) pages 385 to 394, reports total monoterpene concentrations from about 0.01 to about 0.5 ppbv (parts per billion by volume) during day time and from about 0.2 to about 8 ppbv during night time. Taking into account the law of perfect gases and a molecular weight of 136 g/mol for monoterpenes, these correspond to concentrations from about 0.05 to about 2.8 ng/l or 0.05 to about 2.8 micrograms per cubic meter during day time; and from about 1.1 to about 44.5 ng/l or from about 1.1 to 44.5 micrograms per cubic meter during night.

Furthermore, the proportion of individual monoterpenes may vary from one tree species to another tree species. Hence for example, the part of alpha-pinene in the total amount of monoterpene emitted by trees may be from about 0 (2) to about 100% by weight (wt %), whereas the number between parenthesis refers to the lowest measured value published in (S. Moukhtar, Thesis, Institur National Polytechnique de Toulouse, 2005). The corresponding ranges for the most important monoterpenes are listed below in wt %, according to the same source: Alpha-pinene (from about 0 (3.9) to about 55 wt %); Delta-3-carene (from about 0 (0.1) to about 30 wt %); Camphene (from about 0 (1,1) to about 25 wt %); Limonene (from about 0 (0.1) to about 90 wt %); Myrcene (from about 0 (0.4) to about 55 wt %); Sabinene (from about 0 (0.7) to about 75 wt %); Trans-ocimene (from about 0 (14.7) to about 50 wt %); Para-cimene (from about 0 (0.1) to about 20 wt %); Terpinolene (from about 0 (0.5) to about 16 wt %); Alpha-terpineol (from about 0 (0.5) to about 20 wt %).

To illustrate this point, for example, a forest field homogenously populated with *Pinus Sylvestris* may emit a mixture of monoterpenes consisting of about 52 wt % alpha-pinene, about 8 wt % beta-pinene, about 26 wt % delta-3-carene, about 7 wt % camphene, about 4 wt % limonene and about 4 wt % myrcene, in average, whereas a forest field homogeneously populated with *Quercis Robur* may emit about 35 wt % alpha-pinene, about 6 wt % beta-pinene, about 0.3 wt % delta-3-carene, about 6.8 wt % camphene, about 13 wt % limonene, bout 0.5 wt % myrcene, about 0.7 wt % sabinene, about 15 wt % trans-ocimene, about 12 wt % para-cimene and about 12% terpinolene, in average; and *Fagus Sylvatica* may emit 3 wt % alpha-pinene, about 8.5 wt % beta-pinene, about 3 wt % limonene, about 3 wt % myrcene, about 75 wt % sabinene, about 1.5 wt % alpha-thujene, about 8 wt % alpha-phellandrene, about 7.5 wt % gamma-terpinolene and about 1 wt % terpinolene.

Together with concentration of phytoncides, another characteristic of interest for the present disclosure is the rate of emission of phytoncides in nature. This rate is usually expressed in microgram phytoncide per gram of dry wood matter and per hour at 303 K. By definition, the mass of dry wood matter is determined after elimination of water at 60° C. until mass constancy is reached. For most trees, the emission rates of total monoterpenes is from about 0.1 to about 50 micrograms per gram dry matter per hour, depending on the season (J. Llusia, J. Penuelas, American J. Botany, 87 (2000) pages 133 to 140), in another embodiment from about 0.1 mg/h to about 15 micrograms per gram dry matter per hour and in another embodiment from about 0.1 mg/h to about 5 micrograms per gram dry matter per hour (S. Moukhtar, Thesis, Institur National Polytechnique de Toulouse, 2005). On the other hand a living tree is made of from about 50 to about 75 wt % of water, which means that a living tree has from about 25% to 50% dry wood matter. A typical forest of coniferous tree, such as *Pinus Sylvestris*, has a wet biomass of about 1000 kg /m2 (see G. Allwine et al. in "Application of Atmospheric Tracer Technique to Determine Biogenic Hydrocarbon Fluxes from an Oak Forest", B. A. Hutchinson and B. B. Hicks (eds), D Reidel Publishing Company, 1985, pages 361 to 382), which corresponds to a dry matter of 250 to 500 kg. The total amount of monoterpene emitted by this biomass is therefore from about 25 to about 25000 mg per m2/hour, in another embodiment from about 25 to about 7500 mg per m2 per hour, and in another embodiment from about 25 to about 2500 mg per m2 per hour. However, flux measurements performed by G. Allwine (op cit.) show that measured emission values are much less than these values, suggesting dilution factors of from about 30 to 800, due to the action of external wind and vertical convection/diffusion effects. Applying such dilution factors, the effective local emission values are from about 0.03 to about 30 mg per m2 per hour, in another embodiment from about 0.03 to about 10 mg per m2 per hour and in yet another embodiment from about 0.03 to about 3 mg per m2 and hour. Finally, these values need to be divided by 15, which is the half of the average heights of a tree in meters (see for example University of Arkansas Publication FSA5021), in order to get an approximation of the emission rate in the volume located within 2 m from the ground, i.e. at the location where a person walking in a forest will perceive the phytoncides that are beneficial for him/her. This leads to local emission values at this location of from about 1 to about 1000 micrograms per m3 per hour, in another embodiment from about 1 to about 300 micrograms per m3 per hour, and in another embodiment from about 1 to about 100 micrograms per m3 and hour.

Perfume Compositions

According to the present disclosure, perfume compositions include a mixture of phytoncides, solvents, fragrance ingredients and optionally perfume fillers.

Phytoncides

In accordance with one embodiment, the perfume composition according to the present disclosure may include at least one phytoncide. Suitable phytoncides may have a vapor pressure higher than about 0.001 mm/Hg at 25° C.; in another embodiment higher than about 0.01 mm/Hg at 25° C.; and in another embodiment higher than about 0.1 mm/Hg at 25° C.

However, applicants have found that, in the air freshener context, the vapor pressure of ingredients may advantageously be replaced by their Standard Equilibrium Headspace Concentration ($HS_i^0$).

The standard equilibrium headspace concentration ($HS_i^0$, expressed in microgram/liter (µg/L), refers to the concentration of the ingredient in equilibrium with the condensed form—that is solid or liquid form—of this ingredient at a temperature of 25° C. and under a pressure of 1 atmosphere. It can be measured by using any of the known quantitative headspace analysis techniques in the art. A suitable method is described in Mueller and Lamparsky in Perfumes: Art, Science and Technology, Chapter 6 "The Measurement of Odors" at pages 176-179 (Elsevier 1991).

In one example, $HS_i^0$ may be measured as follows: 500 mg of the test compound is added to a headspace container which is then sealed. The container is then incubated at constant 25° C. until the compound reaches equilibrium between the gas and the liquid phase. A defined volume of this saturated headspace (usually 0.5-1.0 liter) is trapped on a micro filter using Porapak Q as sorbent. After filter extraction with an appropriate solvent (usually 30-100 microliters methyl tertiary butyl ether), an aliquot of the extract is analyzed by GC. Quantification is performed by the external standard calibration method. The concentration in the original headspace can be calculated (in terms of µg/L) from the headspace volume sucked through the micro filter and the aliquot of the filter extract injected into the gas chromatograph. The final headspace concentration value of a given test compound is obtained as the mean value of three independent measurements each. Further information of the technique hereinabove described may be found in the article of Etzweiler, F.; Senn E. and Neuner-Jehle N., Ber. Bunsen-Ges. Phys. Chem. 1984, 88, 578-583.

$HS_i^0$ is related to the vapor pressure of an ingredient through the Ideal Gas Law. Applicants consider that $HS_i^0$ is more accurate than most of the tabulated vapor pressure data available because the tabulated data are estimates that have been calculated by using group contribution models, statistical models or ab-initio models, whereas the headspace concentrations used by applicants has been measured according to well established protocols, as hereinabove mentioned.

Exemplary phytoncides according to the present disclosure may include, but are not limited to (E)-1-methyl-4-(6-methylhepta-2,5-dien-2-yl)cyclohex-1-ene, for example BISABOLENE; (1S,4R)-2,2-dimethyl-3-methylenebicyclo[2.2.1]heptane, for example CAMPHENE; (Z)-4,11,11-trimethyl-8-methylenebicyclo[7.2.0]undec-4-ene, for example CARYOPHYLLENNE; (1S,8aR)-1,4,4,6-tetramethyl-2,3,3a,4,5,8-hexahydro-1H-5,8a-methanoazulene, for example ALPHA CEDRENE; 1-methyl-4-propan-2-ylbenzene, for example CIMENE PARA; 3,7,7-trimethylbicyclo[4.1.0]hept-3-ene, for example DELTA-3-CARENE; 1-methyl-4-(prop-1-en-2-yl)cyclohex-1-ene, for example DIPENTENE; (E)-7,11-dimethyl-3-methylenedodeca-1,6,10-triene, for example FARNESENE; (2S)-1,3,4,5,6,7-hexahydro-1,1,5,5-tetramethyl-2H-2,4a-methanonaphthalene, for example ISOLONGIFOLENE; 1-methyl-4-prop-1-en-2-ylcyclohexene, for example D-LIMONENE; 1-methyl-4-propan-2-ylbenzene, for example PARA CIMENE; 1-methyl-4-propan-2-ylcyclohexene, for example PARA MENTHENE; 7-methyl-3-methyleneocta-1,6-diene, for example MYRCENE; (E)-3,7-dimethylocta-1,3,6-triene, for example OCIMENE; 1-methyl-4-propan-2-ylbenzene, for example ALOOCIMENE; 2,6,6-trimethylbicyclo[3.1.1]hept-2-ene, for example PINENE ALPHA; 6,6-dimethyl-2-methylenebicyclo[3.1.1]heptane, for example (PINENE BETA); (4aS, 8S, 8aS)-4,4,8a-trimethyl-7-methylidene-8-(3-methylidenepent-4-enyl)-2,3,4a,5,6,8-hexahydro-1H-naphthalene, for example SCLARENE; 1-methyl-4-propan-2-ylcyclohexa-1,3-diene, for example TERPINENE ALPHA; 1-methyl-4-propan-2-ylcyclohexa-1,4-diene, for example TERPINENE GAMMA; 1-methyl-4-(propan-2-ylidene)cyclohex-1-ene, for example TERPINOLENE; 2-isopropyl-8-methylenedecahydro-4,7-methanoazulene, for example VETYVENE.

Applicants have found that, for air freshener perfume compositions according to the present disclosure, the concentration in the air is directly proportional to the $HS_i^0$ of the pure phytoncide multiplied by the concentration of this phytoncide in the composition in wt %. As used herein, "volatile phytoncides" means phytoncides having a $HS_i^0$ greater than about 1000 µg/L (i.e. vapor pressures higher than about 0.1 mmHg at 25° C.). This allows straightforward predictions of the concentration of phytoncides in the air freshener composition that is required to provide the desired phytoncide concentration profile in the air.

The perfume composition may comprise from about 0.1% to about 15%, or any individual number within the range, by weight of the perfume composition of one or more phytoncides. In another embodiment, the perfume composition may comprise at least about 0.6%, by weight of the perfume composition of one or more phytoncides; in another embodiment at least about 0.8%, by weight of the perfume composition of one or more phytoncides; and in yet another embodiment, at least about 1.1%, by weight of the perfume composition of one or more phytoncides.

In one embodiment, the phytoncides include at least about 25 wt % of one or more phytoncides selected from the group consisting of PINENE ALPHA, PINENE BETA and mixtures thereof. In another embodiment, the perfume composition includes at least 35 wt % of one or more phytoncides selected from the group consisting of PINENE ALPHA, PINENE BETA and mixtures thereof. In yet another embodiment, the perfume composition includes at least 50 wt % of one or more phytoncides selected from the group consisting of PINENE ALPHA, PINENE BETA and mixtures thereof.

In another embodiment, the perfume composition includes from about 0.1% to about 0.9 wt % of PINENE ALPHA; from about 0.1 wt % to about 0.9 wt % of PINENE BETA; and from about 0.1 wt % to about 0.9 wt % of one or more phytoncides selected from the group consisting of BISABOLENE, CAMPHENE, CARYOPHYLLENNE, ALPHA CEDRENE, CIMENE PARA, DELTA-3-CARENE, DIPENTENE, D-LIMONENE, FARNESENE, ISOLONGIFOLENE, PARA CIMENE, PARA MENTHENE, MYRCENE, OCIMENE, ALOOCIMENE, SCLARENE, TERPINENE ALPHA, TERPINENE GAMMA, TERPINOLENE, VETYVENE and mixtures thereof. In another embodiment, the perfume composition includes from about 0.3 wt % to about 0.5 wt % of PINENE ALPHA; from about 0.3 wt % to about 0.5 wt % PINENE BETA; and from about 0.3 wt % to about 0.5 wt % of one or more phytoncides selected from the group consisting of BISABOLENE, CAMPHENE, CARYOPHYLLENNE, ALPHA CEDRENE, CIMENE PARA, DELTA-3-CARENE, DIPENTENE, D-LIMONENE, FARNESENE, ISOLONGIFOLENE, PARA CIMENE, PARA MENTHENE, MYRCENE, OCIMENE, ALOOCIMENE, SCLARENE, TERPINENE ALPHA, TERPINENE GAMMA, TERPINOLENE, VETYVENE and mixtures thereof.

In another embodiment, the perfume composition mimics the phytoncide composition emitted by a pine (*Pinus Sylvestris*) forest. In particular, the perfume composition includes from about 0.07 wt % to about 0.9 wt % of PINENE ALPHA; from about 0.02 wt % to about 0.2 wt % of PINENE BETA; from about 0.1 wt % to about 1.1 wt % of DELTA-3-CARENE; from about 0.01 wt % to about 0.1 wt % of CAMPHENE and from about 0.02 wt % to about 0.2 wt % of LIMONENE. In another embodiment, the perfume composition includes from about 0.27 wt % to about 0.4 wt % of PINENE ALPHA; from about 0.07 wt % to about 0.1 wt % of PINENE BETA; from about 0.35 wt % to about 0.5 wt % of DELTA-3-CARENE; from about 0.04 wt % to about 0.1 wt % of CAMPHENE and from about 0.06 wt % to about 0.1 wt % of LIMONENE.

In another embodiment, the perfume composition mimics the phytoncide composition emitted by an oak (*Quercis Robur*) forest. In particular, the perfume composition includes from about 0.03 wt % to about 0.4 wt % of PINENE ALPHA; from about 0.01 wt % to about 0.1 wt % of PINENE BETA; from about 0.03 wt % to about 0.4 wt % of PARA-CIMENE; from about 0.01 wt % to about 0.1 wt % of CAMPHENE; from about 0.05 wt % to about 0.7 wt % of OCIMENE; from about 0.03 wt % to about 0.4 wt % of TERPINOLENE; and from about 0.04 wt % to about 0.4 wt % of LIMONENE. In another embodiment, the perfume composition includes from about 0.13 wt % to about 0.2 wt % of PINENE ALPHA; from about 0.04 wt % to about 0.1 wt % of PINENE BETA; from about 0.12 wt % to about 0.2 wt % of PARA-CIMENE; from about 0.05 wt % to about 1.1 wt % of CAMPHENE; from about 0.21 wt % to about 0.3 wt % of OCIMENE;

from about 0.13 wt % to about 0.2 wt % of TERPINOLENE; and from about 0.14 wt % to about 0.2 wt % of LIMONENE.

Solvents

In accordance with one embodiment, the perfume composition according to the present disclosure may include at least one solvent. Suitable solvents may have vapor pressures up to about 0.5 mmHg (which corresponds to a $HS_i^0$ of up to about 4000 to about 5000 μg/L), depending on molecular weight; in another embodiment, the solvent may have vapor pressures up to about 0.1 mmHg (which corresponds to a $HS_i^0$ of up to about 500 to about 700 μg/L), depending on molecular weight.

Suitable solvents or mixtures of solvents may be include, but not limited to DIPROPYLENE GLYCOL METHYL ETHER, TRIPROPYLENE GLYCOL METHYL ETHER, for example, DOWANOL TPM, available from Dow Chemicals; DIPROPYLENE GLYCOL METHYL ETHER ACETATE, for example DOWANOL DPMA, available from Dow Chemicals; DIPROPYLENE GLYCOL n-PROPYL ETHER, for example DOWANOL DPnP, available from Dow Chemicals; DIPROPYLENE GLYCOL n-BUTYL ETHER, for example DOWANOL DPnB, available from Dow Chemicals; DIPROPYLENE GLYCOL, PROPYLENE GLYCOL, ISOPAR H to Z, available from ExxonMobil Chemicals; mixtures of DIMETHYL GLUTARATE and DIMETHYL ADIPATE mixtures, for example FLEXISOLVE, available from Flexisolve Technology; 2,2-dimethyl-1,3-dioxolane-4-methanol, for example AUGEO-CLEAN MULTI, available from Rhodia; ETHYLENE GLYCOL DIBENZOATE, for example BENZOFLEX P200, available from Eastman; and 3-METHYL-3-METHOXY BUTANOL, available from Kuraray.

In one embodiment, perfume compositions according to the present disclosure include a solvent at a level of from about 10 to about 75 wt %, in another embodiment from about 25 to about 60 wt %, and in yet another embodiment from about 30 to about 50 wt %.

Fragrance Ingredients

In accordance with one embodiment, fragrance ingredients for use in perfume compositions according to the present disclosure may be selected from natural products such as essential oils, absolutes, resinoids, resins, concretes, and synthetic perfume components such as hydrocarbons, alcohols, aldehydes, ketones, ethers, acids, acetals, ketals and nitriles, including saturated and unsaturated compounds, aliphatic, carbocyclic and heterocyclic compounds, or precursors of any of the above. Other examples of odorant compositions which may be used are described in H 1468 (United States Statutory Invention Registration, or in S. Arctander "Perfume and Flavor Chemicals: Volume 1, Allured Publishing Corporation 1969, or any later editions thereof, as well as the IFRA (International Fragrance Research Association) database, and RIFM (Research Institute of Fragrance Materials) database, each of which and hereby incorporated by reference in their entirety.

Suitable fragrance ingredients that are useful in air freshener perfume compositions include, but are not limited to 2-METHYL 2-PENTENOIC ACID (2-methyl-pent-2-enoic acid); ACETOIN (3-hydroxybutan-2-one); ACETOPHENONE EXTRA (acetophenone); AGRUMEX (2-(tert-butyl) cyclohexyl acetate); ALCOHOL C 9 NONYLIC (nonan-1-ol); ALDEHYDE C 10 DECYLIC (decanal); ALDEHYDE C 11 UNDECYLENIC (undec-10-enal); ALDEHYDE C 12 LAURIC (dodecanal); ALDEHYDE C 6 HEXYLIC (Hexan-1-ol); ALDEHYDE C 8 OCTYLIC (octanal); ALDEHYDE C 9 NONYLIC (nonanal); ALICATE (2,6-dimethylheptan-4-yl acetate); ALLYL AMYL GLYCOLATE (allyl2-(isopentyloxy)acetate); ALLYL CYCLOHEXYL PROPIONATE (allyl 3-cyclohexylpropionate); ALLYL HEPTANOATE; AMBERMAX (1,3,4,5,6,7-hexahydro-beta,1,1,5,5-pentamethyl-2H-2,4a-Methanonaphthalene-8-ethanol); AMBRETTOLIDE ((Z)-oxacycloheptadec-10-en-2-one); AMBROFIX® (3a,6,6,9a-tetramethyldodecahydronaphtho[2,1-b]furan); ANETHOLE SYNTHETIC ((E)-1-methoxy -4-(prop-1-en-1-yl)benzene); ANJERUK® (1-phenylethanethiol); APHERMATE (1-(3,3-dimethylcyclohexyl)ethyl formate); AUBEPINE PARA CRESOL (4-methoxybenzaldehyde); AZURONE (7-isopentyl-2H-benzo[b][1,4]dioxepin-3(4H)-one); BENZYL ACETATE; BENZYL ALCOHOL; BICYCLO NONALACTONE (octahydro-2H-chromen-2-one); BORNEOL CRYSTALS ((1S, 2S,4S)-1,7,7-trimethylbicyclo[2.2.1]heptan-2-ol); BUTYL ACETATE (butyl acetate); BUTYL BUTYRO LACTATE (1-butoxy-1-oxopropan-2-yl butanoate); CARVONE LAEVO (2-methyl-5-(prop-1-en-2-yl)cyclohex-2-enone); CASHMERAN® (1,1,2,3,3-pentamethyl-2,3,6,7-tetrahydro-1H-inden-4(5H)-one); CASSYRANE® (5-tert-butyl-2-methyl-5-propyl-2H-furan); CEDRYL METHYL ETHER ((1R,6S,8aS)-6-methoxy-1,4,4,6-tetramethyloctahydro-1H-5,8a-methanoazulene); CETALOX® (3a,6,6,9a-tetramethyl-2,4,5,5a,7,8,9,9b-octahydro-1H-b enzo [e][1]benzofuran); CINNAMALVA (cinnamonitrile); CINNAMIC ALDEHYDE (cinnamaldehyde); CINNAMYL ACETATE (cinnamyl acetate); CITRAL TECH ((E)-3,7-dimethylocta-2,6-dienal); CITRONELLOL (3,7-dimethyloct-6-en-1-ol); CITRONELLYL ACETATE (3,7-dimethyloct-6-en-1-yl acetate); CITRONELLYL OXYACETALDEHYDE (2-((3, 7-dimethyloct-6-en-1-yl)oxy)acetaldehyde);

CONIFERAN® (2-(tert-pentyl)cyclohexyl acetate); COUMARIN (2H-chromen-2-one); CYCLAL C (2,4-dimethylcyclohex-3-enecarbaldehyde); CYCLAMEN ALDEHYDE (3-(4-isopropylphenyl)-2-methylpropanal); CYCLOGALBANATE (allyl 2-(cyclohexyloxy)acetate); CYCLOHEXAL (4-(4-hydroxy-4-methylpentyl)cyclohex-3-enecarbaldehyde); CYMENE PARA (p-cymene); CYPRISATE (methyl 1,4-dimethylcyclohexanecarboxylate); DAMASCENONE ((E)-1-(2,6,6-trimethylcyclohexa-1,3-dien-1-yl)but-2-en-1-one); DAMASCONE ALPHA ((E)-1-(2,6,6-trimethylcyclohex-2-en-1-yl)but-2-en-1-one);
DAMASCONE DELTA ((E)-1-(2,6,6-trimethyl cyclohex-3-en-1-yl)but-2-en-1-one); DECALACTONE GAMMA (5-hexyloxolan-2-one); DECENAL-4-TRANS ((E)-dec-4-enal); DIETHYL MALONATE; DIHYDRO EUGENOL (2-methoxy-4-propylphenol); DIHYDRO LINALOOL (3,7-dimethyloct-6-en-3-ol); DIHYDRO MYRCENOL (2,6-dimethyloct-7-en-2-ol); DIMETOL (2,6-dimethylheptan-2-ol); DIMETHYL BENZYL CARBINYL ACETATE (2-methyl-1-phenylpropan-2-yl acetate); DIMETHYL BENZYL CARBINYL BUTYRATE (2-methyl-1-phenyl-propan-2-yl butanoate; DIMYRCETOL (2,6-dimethyloct-7-en-2-ol); DODECALACTONE DELTA (6-heptyltetrahydro-2H-pyran-2-one); EBANOL® ((E)-3-methyl-5-(2,2,3-trimethylcyclopent-3-en-1-yl)pent-4-en-2-ol); ELINTAAL (3-(1-ethoxy ethoxy)-3,7-dimethylocta-1,6-diene); ETHYL ACETOACETATE; ETHYL BUTYRATE (ethyl butanoate); ETHYL HEPTANOATE; ETHYL ISOAMYL KETONE (6-methylheptan-3-one); ETHYL ISOVALERATE (ethyl 3-methylbutanoate); ETHYL LINALOOL ((E)-3,7-dimethylnona-1,6-dien-3-ol); ETHYL MALTOL (2-ethyl-3-hydroxy-4H-pyran-4-one); ETHYL METHYL-2-BUTYRATE (ethyl 2-methylbutanoate); ETHYL SAFRANATE (ethyl 2,6,6-trimethylcyclohexa-1,3-diene-1-carboxylate); ETHYL VANILLIN (3-ethoxy-4-hydroxybenzaldehyde); EUCALYPTOL ((1s,4s)-1,3,3-trimethyl-2-oxabicyclo[2.2.2]octane); EUGENOL (4-allyl-2-methoxyphenol); EVERNYL (methyl 2,4-dihydroxy-3,6-dimethylbenzoate); FENCHYL ALCOHOL ((1S,2R,4R)-1,3,3-trimethylbicyclo[2.2.1]heptan-2-ol); FLORALOZONE® (3-(4-ethylphenyl)-2,2-dimethylpropanal); FLORHYDRAL® (3-(3-isopropylpheny)butanal); FLORIDILE® ((E)-undec-9-enenitrile); FLOROCYCLENE (3aR,6S,7aS)-3a,4,5,6,7,7a-hexahy dro-1H-4,7-methanoinden-6-yl propionate); FLOROPAL® (2,4,6-trimethyl-4-phenyl-1,3-dioxane); FLOROSA (tetrahydro-4-methyl-2-(2-methylpropyl)-2H-pyran-4-ol); GALBANONE (1-(3,3-dimethylcyclohex-1-en-1-yl)pent-4-en-1-one); GARDENOL (1-phenylethyl acetate); GARDOCYCLENE (to (3aR,6S, 7aS)-3a,4,5,6,7,7a-hexahydro-1H-4,7-methanoinden-6-yl isobutanoate); GERANIOL ((E)-3,7-dimethylocta-2,6-dien-1-ol); HEDIONE (methyl 3-oxo-2-pentylcyclopentaneacetate); HELIOTROPINE CRYSTALS (benzo[d][1,3]dioxole-5-carbaldehyde); HEXENYL ACETATE CIS-3 (cis-hex-3-enyl acetate); HEXENYL-3-CIS BENZOATE ((Z)-hex-3-en-1-yl benzoate); HEXENYL-3-CIS SALICYLATE ((Z)-hex-3-en-1-yl 2-hydroxybenzoate); HEXYL BUTYRATE (hexyl butanoate); HEXYLIS OBUTYRATE (hexyl isobutanoate); IONONE BETA ((E)-4-(2,6,6-trimethylcyclohex-1-en-1-yl)but-3-en-2-one); IRISONE PURE ((E)-4-(2,6,6-trimethylcyclohex-2-en-1-yl)but-3-en-2-one); ISO E SUPER® (1-(2,3,8,8-tetramethyl-1,2,3,4,5,6,7,8-octahydronaphthalen-2-yl)ethanone); ISOAMYL BUTYRATE (isopentyl butanoate); ISOCYCLOCITRAL (2,4,6-trimethylcyclohex-3-enecarbaldehyde); ISOEUGENOL ((E)-2-methoxy -4-(prop-1-en-1-yl)phenol); ISOMENTHONE DL (2-isopropyl-5-methylcyclohexanone); ISOPENTYL ISOVALERATE (isopentyl 3-methylbutanoate); ISOPROPYL-2 METHYL-4 THIAZOLE (2-isopropyl-4-methylthiazole); ISORALDEINE® 70 ((E)-3-methyl-4-(2,6,6-trimethylcyclohex-2-en-1-yl)but-3-en-2-one); JAMACYCLENE ((3aR,6S,7aS)-3a,4,5,6,7,7a-hexahydro-1H-4,7-methanoinden-6-yl acetate); JASMATONE® (2-hexylcyclopentanone); JASMONYL ((3-pentyloxan-4-yl) acetate); JAVANOL® ((1-methyl-2-((1,2,2-trimethylbicyclo[3.1.0]hexan-3-yl)methyl)cyclopropyl)methanol);
KOHINOOL® (3,4,5,6,6-pentamethylheptan-2-ol); LABIENOXIME ((3E,6E)-2,4,4,7-tetramethylnona-6,8-dien-3-one oxime); LEMONILE® ((2E,6Z)-3,7-dimethylnona-2,6-dienenitrile); LIFFAROME® ((Z)-hex-3-en-1-yl methyl carbonate); LINALOOL (3,7-dimethylocta-1,6-dien-3-ol); LINALYL ACETATE (3,7-dimethylocta-1,6-dien-3-yl acetate); MACEAL (bicyclo[2.2.2]oct-5-ene-2-carboxaldehyde); MAHONIAL ((4E)-9-hydroxy-5,9-dimethyl-4-decenal); MANZANATE (ethyl 2-methylpentanoate); MENTHOL (2-isopropyl-5-methylcyclohexanol); METHOXY PHENYL BUTANONE (4-(4-methoxyphenyl)butan-2-one); METHYL AMYL KETONE (heptan-2-one); METHYL ANTHRANILATE (methyl 2-aminobenzoate); METHYL CINNAMATE (methyl cinnamate); METHYL HEPTENONE (6-methylhept-5-en-2-one); METHYL HEXYL KETONE (octan-2-one); METHYL PAMPLEMOUSSE® (6,6-dimethoxy-2,5,5-trimethylhex-2-ene); MUSK C14 (1,4-dioxacyclohexadecane-5,16-dione); MYRCENE 90 (7-methyl-3-methyleneocta-1,6-diene); NEOFOLIONE ((E)-methyl non-2-enoate); NONANYL ACETATE; OPALAL (7-isopropyl-8,8-dimethyl-6,10-dioxaspiro[4.5]decane); ORANGER CRYSTALS (1-(2-naphtalenyl)-ethanone); OXANE® 50%/TEC (2-methyl-4-propyl-1,3-oxathiane); OXYOCTALINE FORMATE (2,4a,5,8a-tetramethyl-1,2,3,4,4a,7,8,8a-octahydronaphthalen-1-yl formate); PARADISAMIDE® (2-ethyl-N-methyl-N-(m-tolyl)butanamide); PARA-TERT-BUTYL-CYCLOHEXYL ACETATE (4-(tert-butyl)cyclohexyl acetate); PEACH PURE (5-heptyldihydrofuran-2(3H)-one); PELARGOL (3,7-dimethyloctan-1-ol); PETALIA (2-cyclohexylidene-2-(o-tolyl)acetonitrile); PHENOXY ACETALDEHYDE (2-phenoxyacetaldehyde); PHENYL ETHYL ALCOHOL (2-phenylethanol); PRUNOLIDE (5-pentyldihydrofuran-2(3H)-one); RADJANOL® ((E)-2-ethyl-4-(2,2,3-trimethylcyclopent-3-en-1-yl)but-2-en-1-ol); RASPBERRY KETONE (N112) (4-(4-hydroxyphenyl)butan-2-one); RESEDAL (2-(cyclohexylmethyl)-4,4,6-trimethyl-1,3-dioxane); RHUBAFURAN® (2,4-dimethyl-4-phenyltetrahydrofuran); SERENOLIDE (2-(1-(3,3-dimethylcyclohexyl)ethoxy)-2-methylpropyl cyclopropanecarboxylate); ROSSITOL (3-isobutyl-1-methylcyclohexanol); ROSYFOLIA (1-methyl-2-(5-methylhex-4-en-2-yl)cyclopropyl)-methanol); STRAWBERRY PURE (ethyl methyl phenyl glycidate); SYLKOLIDE® ((E)-2-((3,5-dimethylhex-3-en-2-yl)oxy)-2-methylpropyl cyclopropane-carboxylate); TETRAHYDRO LINALOOL (3,7-dimethyloctan-3-ol); TETRAHYDRO MYRCENOL (2,6-dimethyloctan-2-ol); TERPENYL ACETATE (2-(4-methyl cyclohex-3-en-1-yl) propan-2-yl acetate); TERPINEOL (2-(4 -methylcyclohex-3-en-1-yl)propan-2 -ol), THYMOL CRYSTALS (2-isopropyl-5-methylphenol); TRANS-2-HEXENAL (E-hex-2-enal); TRICYCLAL (2,4-dimethylcyclohex-3-enecarbaldehyde); TRIFERNAL (3-phenylbutanal); TRIMOFIX O® (1-((2E,5Z,9Z)-2,7,8-trimethylcyclododeca-2,5,9-trien-1-yl)ethanone); UNDECAVERTOL ((E)-4-methyldec-3-en-5-ol); VANILLIN (4-hydroxy -3-methoxybenzaldehyde); ZINARINE® (2-(2,4-dimethylcyclohexyl)pyridine); and 3-(4-isobutyl-2-methylphenyl)propanal; ADOXAL (2,6,10-trimethylundec-9-enal); CALONE (7-methyl-2H-benzo[b][1,4]dioxepin-3(4H)-one); METHYL OCTYNE CARBONATE (methyl non-2-ynoate); SCENTENAL ((3aR,4R,6S, 7R,7aR)-6-methoxyoetahydro-1H-4,7-methanoindene-1-carbaldehyde); TANAISONE ((Z)-1-(cyclooct-3-en-1-yl)ethanone); FOLIONE (methyl oct-2-ynoate).

The total amount of the one or more fragrance ingredients may be from about 10% to about 80%, or any individual number within the range, by weight of the perfume composition. In another embodiment, the one or more fragrance ingredients may be present in an amount from about 20% to about 60%, by weight of the perfume composition; and in yet another embodiment, the one or more fragrance ingredients may be present in an amount from about 30% to about 50%, by weight of the perfume composition.

Applicants have discovered that, in order to deliver certain phytoncides having a high vapour pressure, such as the monoterpenes mentioned herein above, into the air via an air freshener, the perfume composition must comply with certain design rules. In particular, the applicants have found that the distribution of certain perfume composition ingredients, including solvents and fragrance ingredients, is a key parameter governing the rate of evaporation of the volatile phytoncides. Surprisingly, the applicants have found that, using a certain distribution of perfume composition ingredients having Standard Equilibrium Headspace Concentrations ($HS_i^o$) in the range of from about 1 to about 3000 µg/L, it was possible to control the release of volatile phytoncides having $HS_i^o$ concentrations higher than 30,000 µg/L.

In one embodiment, the perfume mixture exhibits a Standard Equilibrium Headspace Concentration ($HS_i^o$) distribution curve having greater than about 95 wt % of perfume composition ingredients selected from solvents and fragrance ingredients exhibiting a $HS_i^o$ of less than or equal to about 10,000 µg/L; from about 40 wt % to about 85 wt % of perfume composition ingredients selected from solvents and fragrance ingredients exhibiting a $HS_i^o$ of less than or equal to about 1,000 µg/L; from about 20 wt % to about 75 wt % of perfume composition ingredients selected from solvents and fragrance ingredients exhibiting a $HS_i^o$ of less than or equal to about 300 µg/L; and from about 10 wt % to about 50 wt % of perfume composition ingredients selected from solvents and fragrance ingredients exhibiting a $HS_i^o$ of less than or equal to about 100 µg/L.

In another embodiment, the perfume mixture exhibits a Standard Equilibrium Headspace Concentration ($HS_i^o$) distribution curve having greater than about either 95 wt % or 97 wt % of perfume composition ingredients selected from solvents and fragrance ingredients exhibiting a $HS_i^o$ of less than or equal to about 10,000 µg/L; from about 40 wt % to about 85 wt % or from about 55 wt % to about 80 wt % of perfume composition ingredients selected from solvents and fragrance ingredients exhibiting a $HS_i^o$ of less than or equal to about 1,000 µg/L; from about 20 wt % to about 75 wt % or from about 40 wt % to about 60 wt % of perfume composition ingredients selected from solvents and fragrance ingredients exhibiting a $HS_i^o$ of less than or equal to about 300 µg/L; and from about 10 wt % to about 50 wt % or from about 10 wt % to about 25 wt % of perfume composition ingredients selected from solvents and fragrance ingredients exhibiting a $HS_i^o$ of less than or equal to about 100 µg/L.

Suitable perfume composition ingredients having a $HS_i^o$ from about 1,000 to about 10,000 µg/L include, but are not limited to, (2S,4S)-1,7,7-trimethylbicyclo[2.2.1]heptan-2-yl acetate; for example BORNYL ACETATE ($HS_i^o$=1021 µg/L); 3,7-dimethyloctan-3-ol, for example, TETRAHYDRO LINALOOL ($HS_i^o$=1120 µg/L); 2,6-dimethyloct-7-en-2-ol, for example, DIHYDRO MYRCENOL ($HS_i^o$=1200 µg/L); 3,7-dimethylocta-1,6-dien-3-ol, for example, LINALOOL ($HS_i^o$=1408 µg/L); diethyl propanedioate, for example, DIETHYL MALONATE ($HS_i^o$=1529 µg/L); DIPROPYLENE GLYCOL METHYL ETHER, for example, DOWANOL DPM ($HS_i^o$=1758 µg/L); 2,6-dimethyloct-7-en-2-ol, for example DIMYRCETOL ($HS_i^o$=1823 µg/L); 2-(sec-butyl)cyclohexanone, for example, FRESKOMENTHE ($HS_i^o$=1357 µg/L); NONANYL ACETATE ($HS_i^o$=1963 µg/L); 6,6-dimethoxy-2,5,5-trimethylhex-2-ene, for example METHYL PAMPLEMOUSSE ($HS_i^o$=2464 µg/L); ethyl heptanoate, for example, ETHYL OENANTHATE ($HS_i^o$=4356 µg/L); ethyl 3-oxobutanoate, for example ETHYL ACETOACETATE ($HS_i^o$=4767 µg/L); HEXYL ACETATE ($HS_i^o$=8889 µg/L).

Suitable perfume composition ingredients having a $HS_i^o$ from about 300 to about 1,000 µg/L include, but are not limited to 2-(4-methylcyclohex-3-en-1-yl)propan-2-ol, for example, TERPINEOL PURE ($HS_i^o$=312 µg/L); 4-(tert-butyl)cyclohexyl acetate, for example, PARA-TERT-BUTYL-CYCLOHEXYL ACETATE ($HS_i^o$=484 µg/L); phenylmethanol, for example, BENZYL ALCOHOL EXTRA ($HS_i^o$=432 µg/L); 2-(4-methylcyclohex-3-en-1-yl propan-2-yl acetate, for example, TERPINYL ACETATE ($HS_i^o$=466 µg/L); (E)-3,7-dimethylnona-1,6-dien-3-ol, for example, ETHYL LINALOOL ($HS_i^o$=557 µg/L); 2,6-dimethyloctan-2-ol, for example, TETRAHYDRO MYRCENOL ($HS_i^o$=706 µg/L); 3,7-dimethyloct-6-en-3-ol, for example, DIHYDRO LINALOOL ($HS_i^o$=744 µg/L); 1-phenylethyl acetate, for example GARDENOL ($HS_i^o$=761 µg/L); 2-(tert-butyl)cyclohexyl acetate, for example, AGRUMEX ($HS_i^o$=773 µg/L); BENZYL ACETATE ($HS_i^o$=931 µg/L); DIPROPYLENE GLYCOL METHYL ETHER ACETATE, for example DOWANOL DPMA ($HS_i^o$=935 µg/L); 3,7-dimethylocta-1,6-dien-3-yl acetate, for example, LINALYL ACETATE ($HS_i^o$=946 µg/L.

Suitable perfume composition ingredients having a $HS_i^o$ from about 100 to about 300 µg/L include, but are not limited to (3aR,6S,7aS)-3a,4,5,6,7,7a-hexahydro-1H-4,7-methanoinden-6-yl propionate, for example, FLOROCYCLENE ($HS_i^o$=108 µg/L); (3aR,6S,7aS)-3a,4,5,6,7,7a-hexahydro-1H-4,7-methanoinden-6-yl acetate, for example, JASMACYCLENE ($HS_i^o$=211 µg/L); 2-phenylethanol, for example, PHENYL ETHYL ALCOHOL ($HS_i^o$=298 µg/L); TRIPROPYLENE GLYCOL METHYL ETHER, for example, DOWANOL TPM ($HS_i^o$=122 µg/L); mixtures of DIMETHYL GLUTARATE and DIMETHYL ADIPATE mixtures, for example, FLEXISOLVE, available from Flexisolve Technology (average $HS_i^o$=263 µg/L).

Suitable perfume composition ingredients having a $HS_i^o$ less than or equal to about 100 µg/L include, but are not limited to DIPROPYLENE GLYCOL n-BUTYL ETHER, for example, DOWANOL DPnB ($HS_i^o$=21 µg/L) available from Dow Chemicals; tetrahydro-4-methyl-2-(2-methylpropyl)-2H-pyran-4-ol, for example FLOROSA HC($HS_i^o$=99 µg/L); DIPROPYLENE GLYCOL ($HS_i^o$=70 µg/L); methyl 3-phenylprop-2-enoate, for example, METHYL CINNAMATE ($HS_i^o$=73 µg/L); (3-pentyloxan-4-yl) acetate, for example JASMONYL ($HS_i^o$=94 µg/L).

Optional Ingredients

The perfume compositions may, optionally, include additional ingredients which include, but are not limited to, thickeners, gellants, viscosity/gel strength modifiers, solvents, stabilizers, surfactants, chelants, oxidizing agents and UV blockers depending on the method of use.

Air Freshener Devices

The term "air freshener device" includes any suitable surface that allows for at least some evaporation of volatile materials. Any suitable air freshener device having any suitable size, shape, form, or configuration can be used. Suitable air freshener devices can be made from any suitable material, including but not limited to: natural materials, man-made materials, fibrous materials, non-fibrous materials, porous materials, non-porous materials, and combinations thereof. In certain embodiments, the air freshener devices used herein are flameless in character and include any device used for dispensing any type of volatile material (e.g. liquids) into the atmosphere (such as fragrance, deodorant, disinfectant or insecticide active agent). In certain non-limiting embodiments, a typical air freshener device utilizes a combination of a wick, gel, and/or porous surface, and an emanating region to dispense a volatile liquid from a liquid fluid reservoir.

In one embodiment, the air freshener device is an electrical liquid wick air freshener device. An electrical liquid wick air freshener device or liquid electrical wick air freshener refers to device or system that includes an electrical or battery operated source of energy which includes heated liquid wick delivery systems, piezoelectrical spraying systems, electrospray devices or Venturi devices. In another embodiment, the air freshener device is a passive air freshener.

Electrical liquid wick air freshener devices are known for dispensing volatile liquids into the atmosphere, such as fragrance. A typical air freshener device utilizes a combination of a wick and emanating region to dispense a volatile liquid from a liquid fluid reservoir. Ideally, the air freshener device should require little or no maintenance and should perform in a manner that allows the volatile material to be dispensed at a steady and controlled rate into the designated area while maintaining its emission integrity over the life span of the device. During this life span, it is expected that the following conditions are fulfilled: (i) the rate of perfume release into the atmosphere is continuous and nearly constant, i.e. the rate release does not change significantly with time, (ii) the profile of the perfume remains nearly constant, i.e. the odor character of the perfume remains essentially unchanged over time and (iii) the perfume is released in such a way that the totality of the perfume has evaporated during the lifetime of the air freshener, i.e. there is no perfume residue left in the device.

However, the above mentioned conditions are not easily fulfilled. A principal difficulty with air fresheners is to obtain constant release of odorants over the whole life of the device. This is due mainly to the fact that perfume ingredients have vapor pressures covering several orders of magnitude, for example from 0.0001 to 10 and more mmHg at 25° C. Hence, differential evaporation of the ingredient occurs often, where the most volatile ingredients are exhausted much faster from an air freshener device than the less volatile ones, leading to undesired distortion of the perfume character over time. For example, when evaporating from an air freshener device, a perfume having a citrus-woody character may lose its citrus facet within a few hours or a few days, while the less fresh and clean woody facet may remain for weeks. This effect is expected to occur with a broad range of phytoncides of the terpene family, which are characterized by a high vapor pressure. This is an additional difficulty the applicants had to resolve in order to obtain an air freshener perfume composition providing the desired rate of phytoncide release over a given time period (for example, 30, 40 or 60 days).

However, in order to take into account regulatory limits applicable to air fresheners for use in closed environments such as rooms, offices and apartments, the evaporation rate of phytoncides according to the present disclosure may be limited to the range between about 0.1 and 100 micrograms per cubic meter per hour. In one embodiment, an air freshener perfume composition according to the present disclosure provides an evaporation rate of phytoncides into an atmosphere in the range of between about 0.1 and about 100 microgram per cubic meter per hour; in another embodiment the evaporation rate may be in the range between about 0.5 and about 50 microgram per cubic meter and per hour; and in yet another embodiment, the evaporation rate may be in the range between about 0.8 and about 10 microgram per cubic meter per hour. In case more than one phytoncide is released into the atmosphere, the evaporation rate mentioned above refers to the total amount on phytoncides in the perfume composition.

In another embodiment, the air freshener device is an aerosol generator operated by the mean of opening a valve in such a way that the air freshener composition, contained in pressurized vessel, is driven through a nozzle and dispersed into the atmosphere in the form of a multitude of droplets. The driving force pushing the composition through the nozzle is the difference of pressure between the inner of the vessel and the atmosphere. The valve may be opened pushing the valve opener by the action of user's finger or by a mechanical camshaft. U.S. Pat. No. 6,644,507 B2, which is incorporated herein in its entirety, discloses a device, where the valve is opened periodically by the mean of a mechanical mechanism driven by a motor. The motor is actuated following the signal of sensor which determines whether the room is being used. Alternatively, the device can have two vessels and a dual nozzle system, which can be also actuated by a motor, such as disclosed in US 20100038452 A1, and incorporated herein in its entirety.

In another embodiment, the aerosol generator is a piezoelectric element, which is applied directly onto the surface of the air freshener composition. Such a device is disclosed in U.S. Pat. No. 7,622,073 B2, which is incorporated herein in its entirety.

EXAMPLES

The following examples are given solely for the purpose of illustration and are not to be construed as limitations of the present invention, as many variations of the invention are possible without departing from the spirit and scope of the present disclosure. Example 2 is a suitable perfume composition for fresheners according to the present disclosure. Example 1 is comparative.

Examples 1 and 2

Perfume Compositions

Two air freshener perfume compositions were prepared. Example 2 has a distribution of $HS_i^0$ according to the present disclosure and a level of phytoncide (PINENE APLHA) equal to 1.1%. The perfume compositions are reported in Table 1.

TABLE 1

| Perfume compositions (Examples 1 and 2) for use in electrical plug-in air fresheners (all numbers are in weight percent (wt %). | | | |
|---|---|---|---|
| | Example 1 | Example 2 | $HS_i^0$ (μg/L) |
| SOLVENTS Tripropylene Glycol Methyl Ether[1] | 38.9 | 23.9 | 123 |

TABLE 1-continued

Perfume compositions (Examples 1 and 2) for use in electrical plug-in air fresheners (all numbers are in weight percent (wt %).

|  | Example 1 | Example 2 | $HS_i^0$ (µg/L) |
|---|---|---|---|
| Dipropylene Glycol Methyl Ether Acetate[2] | 10 | 25 | 935 |
| PHYTONCIDES |  |  |  |
| PINENE ALPHA | 1.1 | 1.1 | >30,000 |
| FRAGRANCE INGREDIENTS |  |  |  |
|  | 5.5 | 10.1 | <100 |
|  | 9.5 | 9.55 | 100-300 |
|  | 15.5 | 10.5 | 300-1000 |
|  | 15.5 | 19.85 | 1000-10000 |
|  | 4 | 0 | 10000-30000 |
|  | 1 | 0 | >30,000 |

[1]DOWANOL TPM (supplied by Dow Chemicals)
[2]DOWANOL DPMA (supplied by Dow Chemicals)

Electrical plug-in air fresheners containing 18 ml of Perfume Compositions (Examples 1 and 2) were weighed at the start (Day 1) and after 10 and 20 days operation at a temperature of 62.5±2.5° C. The % weight loss (as related to the initial weight of the perfume composition) is reported in Table 2.

TABLE 2

|  | % Weight loss after 10 days | % Weight loss after 20 days |
|---|---|---|
| Example 1 | 30 | 55 |
| Example 2 | 27 | 50 |

The evaporation was stopped for Examples 1 and 2 when the weight loss reached approximately 61%. In particular, for Example 1 the evaporation was stopped at day 23 (61.6% weight loss) and for Example 2 the evaporation was stopped at day 26 (61.2% weight loss). The Examples were analysed to determine the amount of phytoncides remaining and is reported in Table 3.

TABLE 3

|  | % Phytoncide Remaining at approx. 61% weight loss | Total % Phytoncide loss |
|---|---|---|
| Example 1 | 0.51 | 82.00 |
| Example 2 | 1.04 | 63.40 |

As is apparent from Tables 2 and 3, Example 1 having a distribution of $HS_i^0$ values outside of the ranges according to the present invention results in a phytoncide loss after 20 days which is too high to guarantee sufficient phytoncide release after, for example two or three additional weeks of electrical plug-in air freshener operation.

Examples 3-6

Preparation of Different Types of Perfume Compositions and Evaluation of Phytoncide Evaporation Rates Four different air freshener perfume compositions (Example 3-6) were prepared according to Example 2 and placed in an electrical plug-in air freshener. Each Example contained 1.1 wt % of phytoncides. Example 3 used a freshly prepared air freshener, while Examples 4-6 used an aged air freshener. In the present context, "aged" means that the electrical plug-in air freshener was used in an open room until a certain weight loss was reached, in the present case 61 wt % and 81 wt %. The total phytoncide emission rate was determined for each Example, based on air concentrations, and is reported in Table 4.

TABLE 4

|  | Phytoncides | Initial phytoncide conc. (%) | Conc. in air (* initial) (** at 61% loss) (µg/m3) | Conc. in air (81% loss) (µg/m3) | $HS_i^0$ (µg/L) | Total Emission Rate at 61% loss (µg/m3) |
|---|---|---|---|---|---|---|
| Ex. 3 | PINENE ALPHA | 1.1 | 8* |  | 31200 | 3.24 |
| Ex. 4 | PINENE ALPHA | 1.1 | 4.4 ± 1.0** |  | 31200 | 2.2 +/− 0.5 |
| Ex. 5 | PINENE ALPHA | 0.4 | 3.8 ± 0.1** |  | 31200 | 2.83 |
|  | PINENE BETA | 0.4 | 2.4 ± 0.4** |  | 19824 |  |
|  | CARYOPHYLLENE | 0.3 | 0.7 ± 0.15** |  | 285 |  |
| Ex. 6 | PINENE ALPHA | 0.4 | 3.2 ± 0.1** | 1.4 ± 0.1 | 31200 | 2.83 |
|  | PINENE BETA | 0.4 | 2.3 ± 0.4** | 1.2 ± 0.4 | 19824 |  |
|  | TERPINENE GAMMA | 0.3 | 1.4 ± 0.2** | 0.5 ± 0.2 | 5140 |  |

Examples 4-6 were prepared and let to evaporate through an electrical plug-in air freshener heated at a temperature of 62.5±2.5° C. for 2 hours and 30 minutes in a 23 m3 booth. The air inside the booth was sampled over the last 30 minutes, at 50 ml/min wherein during this sampling time the phytoncides were trapped into a 6mm glass desorption tube for Gerstel TDS 2+TDS filled with TENAX TA adsorbent. Samples were then thermally desorbed in a Gerstel TDS unit and trapped at −47° C. in a Gerstel CIS unit. The thermal desorption was carried out by heating the sample during 10 minutes using a heating rate of 28° C./min up to 280° C. The cryo-trapped molecules were flash desorbed at 300° C. into a GC Rtx-5 capillary column, using a split injection and the gas chromatographic analysis was performed according to standard procedures. The measured phytoncide concentrations in the 23 cubic meters were converted into values for 100 cubic meters by applying a dilution factor of about 4.3. With respect to Examples 4-6, the electrical plug-in air freshener was allowed to evaporate until 61% of the composition had been lost (i.e. weight loss of 61%).

These examples show that applying the composition rules according to the present disclosure, the total emission rate of the phytoncides and their concentration in the air are within the desired range.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A perfume composition having controlled release of phytoncides in an atmosphere comprising:
   a) at least about 0.6% by weight of at least one phytoncide; and
   b) a perfume mixture including (i) at least one solvent; and (ii) at least one fragrance ingredient, wherein said perfume mixture exhibits a Equilibrium Headspace Concentration ($HS_i^0$) distribution curve having greater than about 95 wt % of the perfume mixture exhibiting $HS_i^0$ of less than or equal to about 10,000 µg/L.

2. The perfume composition according to claim 1, wherein the perfume mixture exhibits a Standard Equilibrium Headspace Concentration ($HS_i^0$) distribution curve from about 40 wt % to about 85 wt % of the perfume mixture exhibiting $HS_i^0$ of less than or equal to about 1,000 µg/L; from about 20 wt % to about 75 wt % of the perfume mixture exhibiting $HS_i^0$ of less than or equal to about 300 µg/L; and from about 5 wt % to about 50 wt % of the perfume mixture exhibiting a $HS_i^0$ of less than or equal to about 100 µg/L.

3. The perfume composition according to claim 2, wherein the perfume mixture having a $HS_i^0$ of from about 300 to about 1,000 µg/L are selected from the group consisting of 2-(4-methylcyclohex-3-en-1-yl)propan-2-ol; 4-(tert-butyl)cyclohexyl acetate; phenylmethanol; 2-(4-methylcyclohex-3-en-1-yl)propan-2-yl acetate; (E)-3,7-dimethylnona-1,6-dien-3-ol; 2,6-dimethyloctan-2-ol; 3,7-dimethyloct-6-en-3-ol; 1-phenylethyl acetate; 2-(tert-butyl)cyclohexyl acetate; benzyl acetate; dipropylene glycol methyl ether acetate; 3,7-dimethylocta-1,6-dien-3-yl acetate; and combinations thereof.

4. The perfume composition according to claim 2, wherein the perfume mixture having a $HS_i^0$ from about 100 to about 300 µg/L are selected from the group consisting of (3aR,6S,7aS)-3a,4,5,6,7,7a-hexahydro-1H-4,7-methanoinden-6-yl propionate; (3aR,6S,7aS)-3a,4,5,6,7,7a-hexahydro-1H-4,7-methanoinden-6-yl acetate; 2-phenylethanol; tripropylene glycol methyl ether; mixtures of dimethyl glutarate and dimethyl adipate; and combinations thereof.

5. The perfume composition according to claim 2, wherein the perfume mixture having a $HS_i^0$ less than or equal to about 100 µg/L are selected from the group consisting of dipropylene glycol n-butyl ether; tetrahydro-4-methyl-2-(2-methylpropyl)-2H-pyran-4-ol; dipropylene glycol; methyl 3-phenylprop-2-enoate; (3-pentyloxan-4-yl) acetate and combinations thereof.

6. The perfume composition according to claim 1, wherein the at least one solvent is selected from the group consisting of dipropylene glycol methyl ether, tripropylene glycol methyl ether; dipropylene glycol methyl ether acetate; dipropylene glycol n-propyl ether; dipropylene glycol n-butyl ether; dipropylene glycol; propylene glycol; isoparaffins; mixtures of dimethyl glutarate and dimethyl adipate; 2,2-dimethyl-1,3-dioxolane-4-methanol; ethylene glycol dibenzoate; 3-methyl-3-methoxy butanol and combinations thereof.

7. The perfume composition according to claim 1, wherein the at least one fragrance ingredient is present in an amount of about 10% to about 80% by weight of the perfume composition.

8. The perfume composition according to claim 1, wherein the perfume mixture having a $HS_i^0$ of from about 1,000 to about 10,000 µg/L are selected from the group consisting of (2S,4S)-1,7,7-trimethylbicyclo[2.2.1]heptan-2-yl acetate; 3,7-dimethyloctan-3-ol; 2,6-dimethyloct-7-en-2-ol; 3,7-dimethylocta-1,6-dien-3-ol; diethyl propanedioate; dipropylene glycol methyl ether; 2-(sec-butyl)cyclohexanone; nonanyl acetate; 6,6-dimethoxy-2,5,5-trimethylhex-2-ene; ethyl heptanoate; ethyl 3-oxobutanoate; hexyl acetate and combinations thereof.

9. The perfume composition according to claim 1 having a phytoncide evaporation rate of from about 0.8 µg/m3 per hour to about 10 µg/m3 per hour that is constant for at least 30 days.

10. The perfume composition according to claim 1, wherein the at least one phytoncide comprises at least one monoterpene or derivative thereof.

11. The perfume composition according to claim 1, wherein the at least one phytoncide comprises at least one sesquiterpene or derivative thereof.

12. The perfume composition according to claim 1, wherein the at least one phytoncide comprises bisabolene, camphene, caryophyllenne, alpha cedrene, delta-3-carene, dipentene, farnesene, isolongifolene, d-limonene, para cymene, para menthene, myrcene, ocimene, aloocimene, sclarene, terpinene alpha, terpinene gamma, terpinolene, vetyvene and/or combinations thereof.

13. The perfume composition according to claim 1, wherein the at least one phytoncide comprises (E)-1-methyl-4-(6-methylhepta-2,5-dien-2-yl)cyclohex-1-ene, (1S,4R)-2,2-dimethyl-3-methylenebicyclo[2.2.1]heptane, (Z)-4,11,11-trimethyl-8-methylenebicyclo[7.2.0]undec-4-ene, (1S,8aR)-1,4,4,6-tetramethyl-2,3,3a,4,5,8-hexahydro-1H-5,8a-methanoazulene, 1-methyl-4-propan-2-ylbenzene, 3,7,7-trimethylbicyclo[4.1.0]hept-3-ene, 1-methyl-4-(prop-1-en-2-yl)cyclohex-1-ene, (E)-7,11-dimethyl-3-methylenedodeca-1,6,10-triene, (2S)-1,3,4,5,6,7-hexahydro-1,1,5,5-tetramethyl-2H-2,4a-methanonaphthalene, 1-methyl-4-prop-1-en-2-ylcyclohexene, 1-methyl-4-propan-2-ylbenzene, 1-methyl-4-propan-2-ylcyclohexene, 7-methyl-3-methyleneocta-1,6-diene, (E)-3,7-dimethylocta-1,3,6-triene, 1-methyl-4-propan-2-ylbenzene, (4aS,8S,8aS)-4,4,8a-trimethyl-7-methylidene-8-(3-methylidenepent-4-enyl)-2,3,4a,5,6,8-hexahydro-1H-naphthalene, 1-methyl-4-propan-2-ylcyclohexa-1,3-diene, 1-methyl-4-propan-2-ylcyclohexa-1,4-diene, 1-methyl-4-(propan-2-ylidene) cyclohex-1-ene, 2-isopropyl-8-methylenedecahydro-4,7-methanoazulene and/or combinations thereof.

14. The perfume composition according to claim 1 comprising at least about 0.8% by weight of the least one phytoncide.

15. The perfume composition according to claim 1 comprising at least about 1.1% by weight of the least one phytoncide.

16. The perfume composition according to claim 1 comprising at least two phytoncides.

17. The perfume composition according to claim 16, wherein the at least two phytoncides comprise a monoterpene and a sesquiterpene.

* * * * *